United States Patent [19]

Gibson

[11] 4,054,377
[45] Oct. 18, 1977

[54] METHOD AND APPARATUS FOR EXAMINING SHEET MATERIAL
[75] Inventor: William Gibson, Newcastle upon Tyne, England
[73] Assignee: Ciba-Geigy AG, Basel, Switzerland
[21] Appl. No.: 640,371
[22] Filed: Dec. 15, 1975
[30] Foreign Application Priority Data
Dec. 19, 1974 United Kingdom ............... 54869/74
[51] Int. Cl.$^2$ ..................... G01N 21/16; G01N 21/18; G01N 21/30; G01N 21/32
[52] U.S. Cl. .................................... 356/199; 250/563; 356/200
[58] Field of Search ............... 356/199, 200, 237, 239; 250/563, 572

[56] References Cited
U.S. PATENT DOCUMENTS 3,496,365  2/1970  Mounce ................................. 250/563
3,565,536  2/1971  Wuellner et al. ..................... 356/239

Primary Examiner—Vincent P. McGraw
Attorney, Agent, or Firm—Karl F. Jorda

[57] ABSTRACT

Method and apparatus for examining sheet material to detect faults therein in which the surface of the sheet material is scanned by a moving beam of electromagnetic radiation which raditation is thereafter directed to a photoelectric cell to produce therefrom a wideband electric signal comprising both high and low frequency components in which the said wideband signal is electronically processed to provide a quotient signal corresponding to the high frequency component divided by the low frequency component and applying said quotient signal to an amplitude discriminator the output of which indicates the presence of a fault in the sheet material by generation a signal of digital form in response to a disturbance in the wideband signal exceeding in amplitude a given proportion of the amplitude of said low frequency component.

7 Claims, 4 Drawing Figures

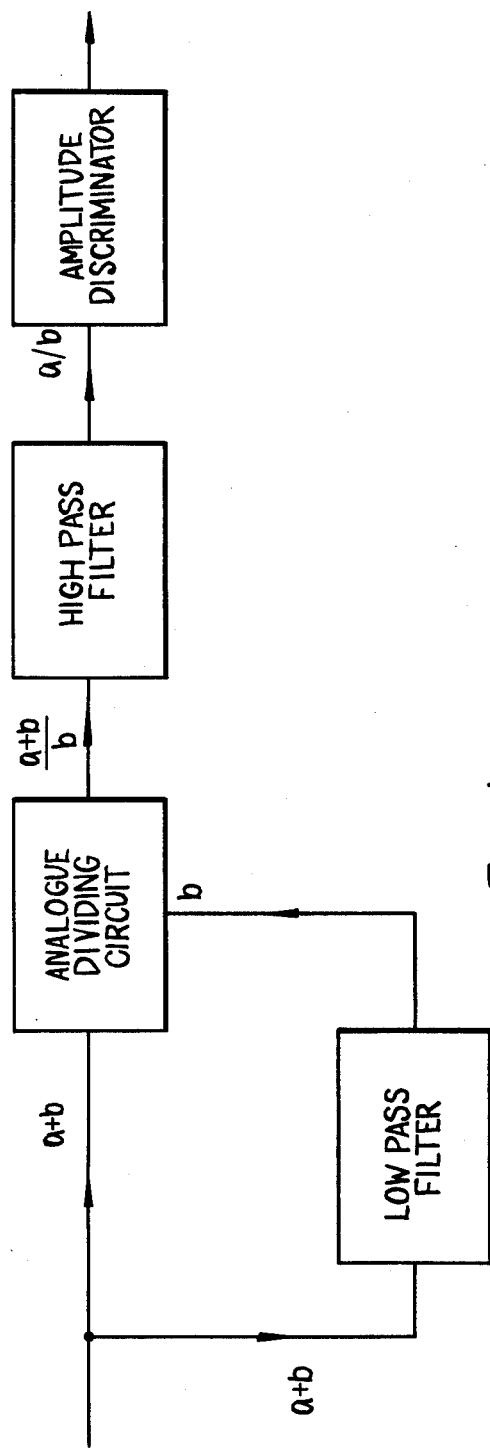

METHOD AND APPARATUS FOR EXAMINING SHEET MATERIAL

This invention relates to a method of scanning sheet material.

The usual method of examining sheet materials such as paper or plastic film materials for faults is to scan across to width of the sheet with a moving light beam and to measure the changing amount of light transmitted through the material or reflected from the surface of the material as the sheet is scanned. A sudden change in the amount of light transmitted or reflected indicates a fault; the material at the position of the fault being either more or less light-absorbing or reflecting than the rest of the sheet. The coverage of the whole sheet is ensured by establishing relative motion between scanning device and the sheet in the direction of the length of the sheet. This is normally achieved by moving the sheet and scanning across the width of the sheet with the beam of light.

The method of measurement of the transmitted or reflected light presents some difficulty since it must not itself introduce variations in the light transmitted or reflected which could be mistaken for faults in the sheet material. The usual devices for measuring variations in the light transmitted or reflected are electronic photodetectors such as photo-multipliers. Such devices normally have an approximately circular light collecting window and thus it is required that a light collecting device be present either under the sheet being scanned in order to convey a constant proportion of the light transmitted by the sheet to the circular window of the photosensitive device or over the sheet to collect the light reflected from the surface of the sheet.

A large number of light guide devices have been suggested and some used but generally such devices suffer from the disadvantages that they would have a non-uniform collection efficiency. In particular the electrical signal produced in response to each scan when using such light guide devices usually is greatest when the middle of the web is being scanned and least when the edges of the material are being scanned. The difference in response is so great that often it becomes impossible to detect small faults which are present towards the edges of the sheet material.

The electrical signal produced in response to each scan when no fault is present on the sheet material during this scan can be considered to be low frequency response. If a fault be present during the scan the electrical signal produced when this fault is being scanned contains the normal low frequency response associated with the position across the sheet at which the fault is located, i.e. higher at the middle of the sheet than at the edges, together with a high frequency response due to the fault which may be of a positive or of a negative sign, i.e. the fault may cause a much greater response or a much smaller response depending on its nature. Thus the electrical signal produced during the scanning of sheet material may be considered as a wideband electrical signal comprising both high and low frequency components.

It is the object of the present invention to provide a method of scanning sheet material by a scanning method and processing the wideband electrical signal received so as to enable small faults which may be present towards the edges of the sheet material to be detected.

According to the present invention there is provided a method of examining sheet material to detect faults therein in which the surface of the sheet material is scanned by a moving beam of electromagnetic radiation which radiation is thereafter directed to a photoelectric cell to produce therefrom a wideband electric signal comprising both high and low frequency components, in which the said wideband signal is electrically processed to provide a quotient signal corresponding to the high frequency component divided by the low frequency component and applying said quotient signal to an amplitude discriminator the output of which indicates the presence of a fault in the sheet material by generation a signal of digital form in response to a disturbance in the wideband signal exceeding in amplitude a given proportion of the amplitude of said low frequency component.

The quotient signal corresponding to the high frequency component divided by the low frequency component may be obtained by feeding the wideband signal to a low pass filter which passes only the low frequency component to the denominator input of an analogue dividing circuit and feeding at least the high frequency component of the wideband signal to the numerator input of said analogue dividing circuit and then passing the so-divided high frequency component to the amplitude discriminator.

In this method the high frequency component of the wideband signal may be obtained by feeding the wideband signal directly to a high-pass filter which passes only the high frequency component to the numerator input of the analogue dividing circuit. Alternatively the wideband signal may be fed directly to the input of the analogue dividing circuit the output of which is fed to a high pass filter to obtain the divided high frequency component which is fed to the said amplitude discriminator.

According to another aspect of the present invention there is provided a device for scanning sheet material by reflection and/or transmission which comprises a light source which scans across the sheet material which is caused to move relative to the light source, a photoelectric cell and means for guiding the light reflected from the surface of the sheet material or transmitted through the sheet material to the photoelectric cell, a low-pass filter which receives the wideband signal from the photo-electric cell and which passes the low frequency component of the wideband signal to the denominator input of an analogue dividing circuit, a high-pass filter which receives the wideband signal from the photoelectric cell and which passes the high frequency component of the wideband signal to the numerator input of the said analogue dividing circuit, an amplitude discriminator which receives the divided high frequency component of the wide band signal from the analogue dividing circuit, said amplitude discriminator being adapted to generate a digital signal in response to a disturbance on the wideband signal which exceeds in amplitude a given proportion of the amplitude of the said low frequency component.

According to another embodiment of this aspect of the present invention there is provided a device for scanning sheet material by reflection and/or transmission which comprises a light source which scans across the sheet material which is caused to move relative to the light source, a photoelectric cell and means for guiding the light reflected from the surface of the sheet material or transmitted through the sheet material to the photoelectric cell, a low-pass filter which receives the wideband signal from the photoelectric cell and passes the low frequency component of the wideband signal to the denominator input of an analogue dividing circuit means for feeding the wideband signal to the numerator input of the said analogue dividing circuit, a high-pass filter which receives the output from the analogue dividing circuit and passes only the high frequency component of the numerator of the quotient signal produced therefrom to an amplitude discriminator which receives the divided high frequency component of the wideband signal from the analogue dividing circuit, said amplitude discriminator being adapted to generate a digital signal in response to a disturbance on the wideband signal which exceeds in amplitude a given proportion of the amplitude of the said low frequency component. Preferably the photocell in both these embodiments is a photomultiplier.

The accompanying drawings will serve to illustrate the invention.

FIG. 4 is a block diagram of the layout of the electronic circuit used in another embodiment of the invention.

Figure 1:
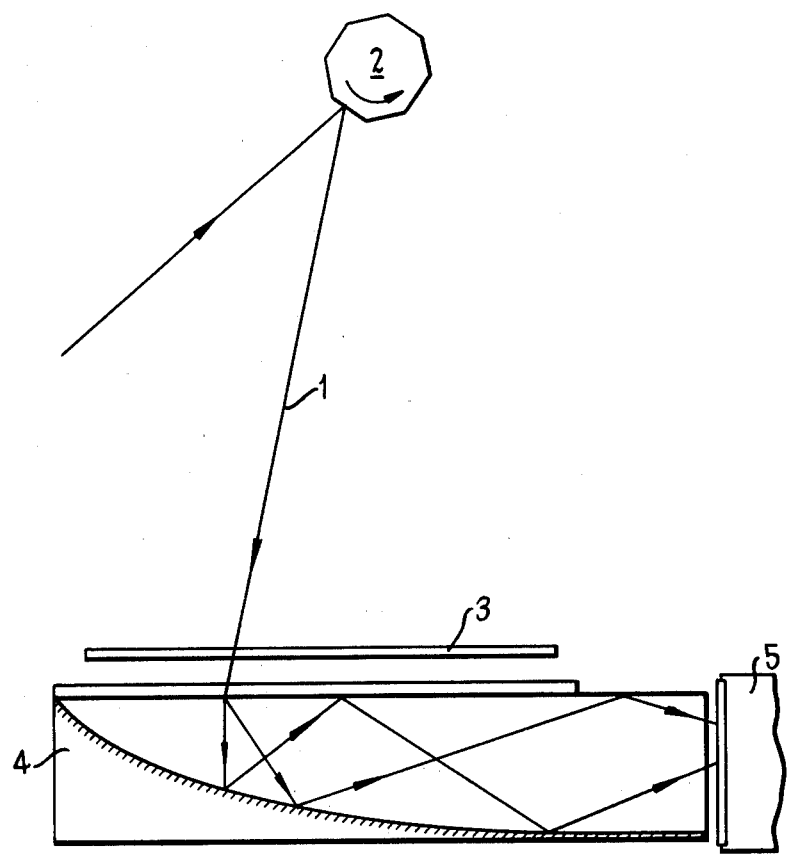
FIG. 1 shows diagramatically a sheet material scanning device in which the scanning light is transmitted through the sheet material and directed to a photocell.

In FIG. 1 a beam of light 1 is reflected from a rotating polygonal mirror drum 2 and is caused to scan across a travelling sheet of material 3. The light transmitted through the sheet of material 3 is directed by the light directing device 4, to a photomultiplier 5.

The output from the photomultiplier 5 is a wideband electrical signal.

Figure 2:
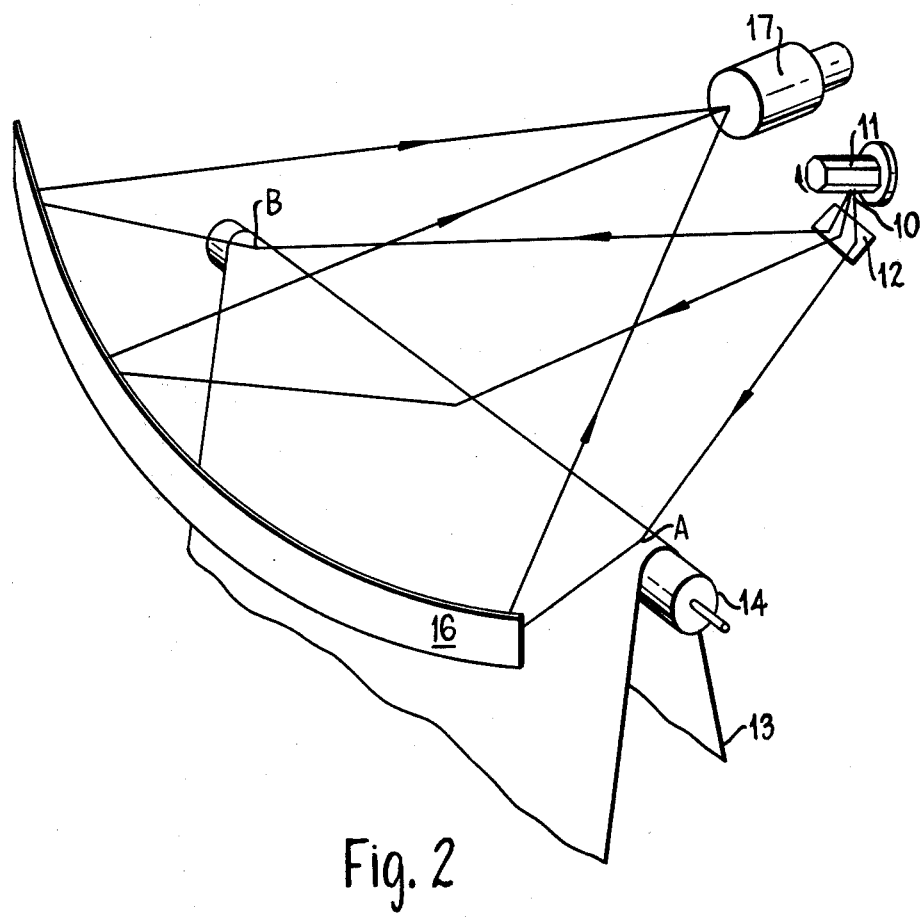
FIG. 2 shows diagramatically a web scanning device in which the scanning light is reflected from the surface of the web and directed to a photocell.

In FIG. 2 a beam of light 10 is reflected from a rotating polygonal mirror drum 11 on to an angled mirror 12 and is caused to scan across a travelling web 13 held in position over a roller 14 along the line A–B. Light reflected from the web strikes the curved mirror 16 and is reflected from there on to the photomultiplier 17. The output from the photomultiplier 17 is a wideband electrical signal.

Figure 3:
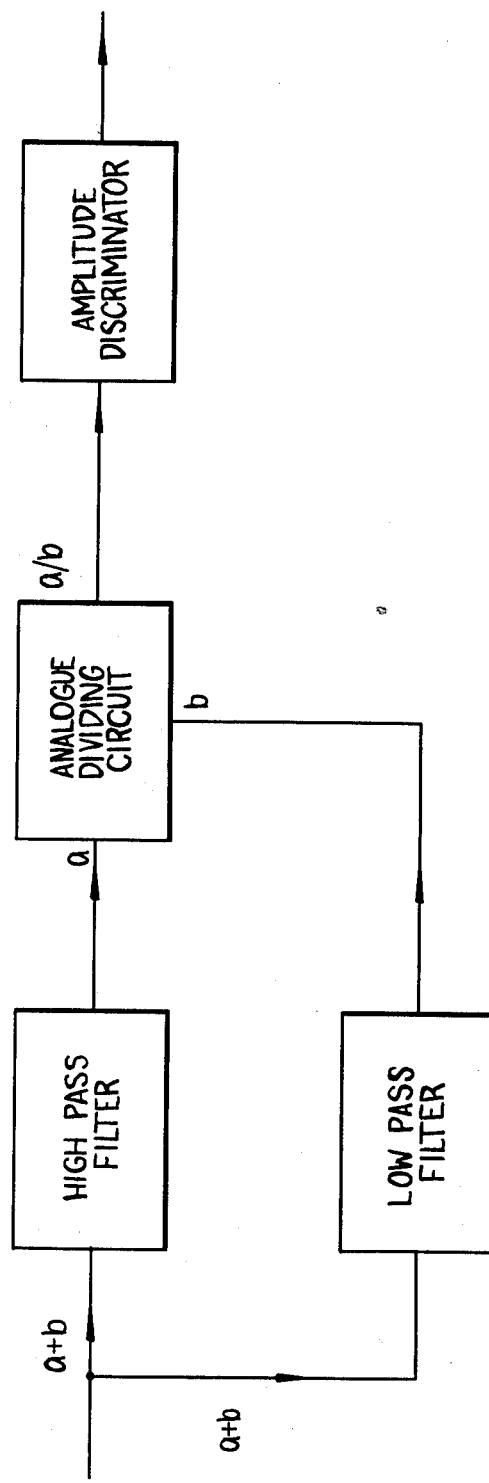
FIG. 3 is a block diagram of the layout of the electronic circuit used in one embodiment of the invention.

In FIG. 3 the wideband electrical signal from either the photomultiplier 5 or the photomultiplier 17 is fed both to a high-pass filter and to a low-pass filter. The output from the high-pass filter is fed to the numerator input of the analogue dividing circuit and the output from the low-pass filter is fed to the denominator input of the analogue dividing circuit. The quotient signal obtained (shown in the Figure as $a/b$) is fed to the input of an amplitude discriminator. The output of the amplitude discriminator is a digital signal when a fault has been scanned which is of such magnitude that it causes a disturbance in the wideband signal obtained from the photomultiplier which exceeds in amplitude a given proportion of the amplitude of the low frequency component shown as b in the figure.

In FIG. 4 the wideband electrical signal from either the photomultiplier 5 or the photomultiplier 17 is fed both to a low-pass filter and to the numerator input of the analogue dividing circuit. The output of the low-pass filter is fed to the denominator input of the analogue dividing circuit. The output of the analogue dividing circuit which is shown in the figure $(a + b/b)$ is fed to the input of a high-pass filter and the output of this filter (shown as $a/b$) is fed to the input of an amplitude discriminator. The same output is obtained from the amplitude discriminator as from the amplitude discriminator of FIG. 3.

The signal from both of the photomultiplier tubes 5 and 17 is proportional both to the efficency of the optical system, and to the transmission (FIG. 1) or reflection (FIG. 2) factor of the web material.

A formula representing this signal can be written:

$$A \cdot \eta(x) \cdot T(x) \tag{1.}$$

where
$A$ is a scaling factor
$\eta(x)$ is the efficiency of the optical system,
$T(x)$ is the transmission or reflection factor,
$x$ represents the position on the material to which the signal corresponds.

Now:

$$T(x) = \overline{T(x)} + \delta T(x)$$

where
$\overline{T(x)}$ is the mean of $T(x)$ and
$\delta T(x)$ is the change in $T(x)$ with position.

Thus 1 becomes:

$$A \cdot \eta(x) \cdot [\overline{T(x)} + \delta T(x)] \tag{2.}$$

The required signal to be obtained from this is that corresponding to the change in transmission or reflection characteristics as a proportion of the mean:

$$\delta T(x)/\overline{T(x)} \tag{3.}$$

This is the signal shown in respect of FIGS. 3 and 4 as $a/b$ which is fed to the amplitude discriminator.

Now with reference to the electronic layout of FIG. 3 Formula 2 may be re-arranged to give:

$$A\eta(x) \overline{T(x)} + A\eta(x) \delta T(x)$$

The left hand term consists of only low frequency terms, thus the output of the low pass filter in FIG. 1 is given by:

$$A\eta(x) \overline{T(x)} \tag{4.}$$

The right hand term consists of only high frequency terms, so the output of the high pass filter in FIG. 1 is:

$$A\eta(x) \delta T(x) \tag{5.}$$

When the two signals 4 and 5 are combined in the divider the signal $$\frac{A\eta(x) \delta T(x)}{A\eta(x) \overline{T(x)}}$$

results, and this may be reduced to $[\delta T(x)/\overline{T(x)}]$ which is the desired output signal.

With reference to the electronic layout of FIG. 4. As in method (a), the signal after the low pass filter is:

$$A\eta(x) \overline{T(x)} \tag{6.}$$

When combined with the input signal in the divider the resulting signal is:

$$\frac{A\eta(x)[\overline{T(x)} + \delta T(x)]}{A\eta(x)\overline{T(x)}}$$

$$= 1 + \frac{\delta T(x)}{\overline{T(x)}}$$

The high pass filter through which this signal has passed removes the constant term leaving: $(\delta T(x)/\overline{T(x)})$ the desired signal.

What is claimed is:

1. A method of examining sheet material to detect faults therein in which the surface of the sheet material is scanned by a moving beam of electromagnetic radiation which radiation is thereafter directed to a photoelectric cell to produce therefrom a wideband electric signal comprising both high and low frequency components in which the said wideband signal is electronically processed to provide a quotient signal corresponding to the high frequency component divided by the low frequency component and applying said quotient signal to an amplitude discriminator the output of which indicates the presence of a fault in the sheet material by generation a signal of digital form in response to a disturbance in the wideband signal exceeding in amplitude a given proportion of the amplitude of said low frequency component.

2. A method according to claim 1 wherein quotient signal corresponding to the high frequency component divided by the low-frequency component is obtained by feeding the wideband signal to a low-pass filter which passes only the low frequency component to the denominator input of an analogue dividing circuit and feeding at least the high frequency component of the wideband signal to the numerator input of said analogue dividing circuit and then passing the so-divided high frequency component to the amplitude discriminator.

3. A method according to claim 2 wherein the high-frequency component of the wideband signal is obtained by feeding the wideband signal directly to a high-pass filter which passes only the high frequency component to the numerator of the analogue dividing circuit.

4. A method according to claim 2 wherein the wideband signal is fed directly to the input of the analogue dividing circuit, the output of which if fed to a high pass filter to obtain the divided high frequency component which is fed to the said amplitude descriminator.

5. A device for scanning sheet material by reflection and/or transmission which comprises a light source which scans across the sheet material which is caused to move relative to the light source, a photo-electric cell and means for guiding the light reflected from the surface of the sheet material or transmitted through the sheet material to the photoelectric cell, a low-pass filter which receives the wideband signal from the photoelectric cell and which passes the low frequency component of the wideband signal to the denominator input of an analogue dividing circuit, a high-pass filter which receives the wideband signal from the photoelectric cell and which passes the high frequency component of the wideband signal to the numerator input of the said analogue dividing circuit, an amplitude discriminator which receives the divided high frequency component of the wideband signal from the analogue dividing circuit, said amplitude discriminator being adapted to generate a digital signal in response to a disturbance on the wideband signal which exceeds in amplitude a given proportion of the amplitude of the said low frequency component.

6. A device for scanning sheet material by reflection and/or transmission which comprises a light source which scans across the sheet material which is caused to move relative to the light source, a photoelectric cell and means for guiding the light reflected from the surface of the sheet material or transmitted through the sheet material to the photoelectric cell, a low-pass filter which receives the wideband signal from the photoelectric cell and passes the low frequency component of the wide-band signal to the denominator input of an analogue dividing circuit means for feeding the wideband signal to the numerator input of the said analogue dividing circuit, a high-pass filter which receives the output from the analogue dividing circuit and passes only the high frequency component of the numerator of the quotient signal produced therefrom to an amplitude discriminator which receives the divided high frequency component of the wideband signal from the analogue dividing circuit, said amplitude discriminator being adapted to generate a digital signal in response to a disturbance on the wideband signal which exceeds in amplitude a given proportion of the amplitude of the said low frequency component.

7. In a method of examining sheet material to detect faults therein in which the surface of the sheet material is scanned by a moving beam of electromagnetic radiation which radiation is thereafter directed to a photoelectric cell to produce therefrom a wideband electric signal comprising both high and low frequency components, the step of electronically processing said wideband signal to provide a quotient signal corresponding to the high frequency component divided by the low frequency component and applying said quotient to an amplitude discriminator the output of which indicates the presence of a fault in the sheet material by generation a signal of digital form in response to a disturbance in the wideband signal exceeding in amplitude a given proportion of the amplitude of said low frequency component.

* * * * *